United States Patent [19]

Schwindt et al.

[11] Patent Number: 6,121,459
[45] Date of Patent: Sep. 19, 2000

[54] SINGLE POT PROCESS FOR PRODUCING (Z)-AZABICYCLO OXIME ETHERS

[75] Inventors: Mark Alan Schwindt, Holland; Lloyd Charles Franklin, Hamilton; Haile Tecle, Ann Arbor, all of Mich.

[73] Assignee: Warner-Lambert Company, Morris Plains, N.J.

[21] Appl. No.: 09/355,227

[22] PCT Filed: Dec. 29, 1997

[86] PCT No.: PCT/US97/23872

§ 371 Date: Dec. 23, 1999

§ 102(e) Date: Dec. 23, 1999

[87] PCT Pub. No.: WO98/32758

PCT Pub. Date: Jul. 30, 1998

Related U.S. Application Data

[60] Provisional application No. 60/035,977, Jan. 27, 1997.

[51] Int. Cl.$^7$ .................................................. C07D 487/08
[52] U.S. Cl. ............................................. 548/453; 546/137
[58] Field of Search ............................... 548/453; 546/137

[56] References Cited

U.S. PATENT DOCUMENTS

| | | |
|---|---|---|
| 4,158,015 | 6/1979 | Paul . |
| 5,306,718 | 4/1994 | Lauffer et al. . |
| 5,318,978 | 6/1994 | Lauffer et al. . |
| 5,346,911 | 9/1994 | Augelli-Szafran et al. . |
| 5,354,883 | 10/1994 | Isak et al. . |

FOREIGN PATENT DOCUMENTS

| | | |
|---|---|---|
| 0 445 731 A1 | 9/1991 | European Pat. Off. . |
| WO 93/08192 | 4/1993 | WIPO . |
| WO 94/13678 | 6/1994 | WIPO . |
| WO 95/34562 | 12/1995 | WIPO . |

OTHER PUBLICATIONS

Bjørgo, J. et al., "Conformational and Electronic Effects on Imine Stereochemistry", *Tetrahedron Letters*, No. 18, pp. 1747–1750 (1972).

Curtin, D. et al., "Uncatalyzed syn–anti Isomerization of Imines, Oxime Ethers, and Haloimines", *J. Am. Chem. Soc.*, vol. 88, pp. 2775–2786 (Jun. 20, 1966).

Hauser, C. et al., "Syn–Anti Isomerism of p–Chlorobenzaldoxime with Boron Fluoride", *J. Org. Chem.*, vol. 20, pp. 1491–1495 (1955).

March, J., "Advanced Organic Chemistry—Reactions, Mechanisms, and Structure" 3rd Edition, pp. 805–806 (1985).

Matlin, S. et al., "Resolution and Identification of Steriod Oxime SYN and Anti Isomers by HPLC", *J. Liquid Chromatography*, vol. 13, No. 17, pp. 3455–3463 (1990).

Murakata, M. et al., "Lipase–catalyzed Kinetic Resolution of Phenylcyclohexanone Oxime Esters", *Tetrahedron: Asymmetruy*, vol. 5, No. 10, pp. 2019–2024 (1994).

Padwa, A. et al., Concentration Effects in the Photochemical Syn–Anti Isomerization of an Oxime Ether, *J. Org. Chem.*, vol. 39, No. 16, pp. 2361–2366 (1974).

Plate et al., "Synthesis and Muscarinic $M_3$ Pharmacological Activities of 1–Azabicyclo[2.2.2]octan–3–one OximeDerivatives", *Bioorganic & Medicinal Chemistry*, vol. 4, No. 2, pp. 239–245 (1996).

Pratt, A. et al., "Photochemistry of the Carbon–Nitrogen Double Bond, Part 1. Carbon–Nitrogen vs. Carbon–Carbon Double Bond Isomerisation in the Photochemistry of α, β–Unsaturated Oxime Ethers: The Benzylideneacetone Oxime O–Methyl Ether System", *J. Chem. Soc.*, Perkin Trans. 1, pp. 1691–1693 (1986).

van Dijk, J. et al., "Oxime Ether Derivatives, a new Class of Nonsteroidal Antiinflammatory Compounds", *J. Med. Chem.*, vol. 20, No. 9, pp. 1199–1206 (1977).

*Primary Examiner*—Robert W. Ramsuer
*Attorney, Agent, or Firm*—Merchant & Gould P.C.

[57] ABSTRACT

Biologically active O-substituted azabicyclo oximes having the Z configuration may be isolated simply, without chromatographic separation, and in high yield and Z/E purity through the coupling of a 1-azabicyclo-3-one with an O-substituted hydroxylamine in acidic aqueous solution and conversion of E-configured isomer to Z-isomer without requiring purification or separation. Neutralization and subsequent isolation of the free base followed by precipitation of the salt allows separation of the Z-isomer with high Z/E purity.

20 Claims, No Drawings

SINGLE POT PROCESS FOR PRODUCING (Z)-AZABICYCLO OXIME ETHERS

This application is a 371 of PCT/US 97/2382 filed Dec. 29, 1997 and claims the benefit of provisional application 60/035,977 filed Jan. 27, 1997.

TECHNICAL FIELD

The present invention pertains to a process of producing and isolating (Z)-azabicyclo oxime ethers in high yield and with excellent isomer purity.

BACKGROUND OF THE INVENTION

Numerous oxime ethers have been shown to have biological activity. See, e.g., U.S. Pat. Nos. 4,158,015; 5,354,883; 5,318,978; and 5,306,718; European published application EP 0 445 731 A1; and PCT published applications WO 93/08192; WO 94/13678; and WO 95/34562; and publications S. A. Matlin et al., "Resolution and Identification of Steroid Oxime Syn and Anti Isomers by HPLC, " *J. LIQUID CHROMATOGRAPHY*, 13 (17), pp. 3455–3463 (1990); and J. van Dijk et al., "Oxime Ether Derivatives, A New Class of Nonsteroidal Antiinflammatory Compounds," *J. MED. CHEM.*, 20 (9), pp. 1199–1206 (1977), all these patents and publications incorporated herein by reference. For example, [R-(Z)]-1-azabicyclo[2.2.1]heptan-3-one, O-[3-(3-methoxyphenyl)-2-propynyl]oxime has been demonstrated to be a muscarinic agonist which is expected to be useful in treating cognitive disorders, including Senile Dementia Alzheimers Type (SDAT). Reference may be had to PCT/US95/05033 (WO 95/34562); U.S. Pat. No. 5,346,911; EP 0 445731 A1; U.S. Pat. No. 5,318,978; U.S. Pat. No. 5,306,718; and PCT/US92/08642 (WO 93/08192), these patents and/or published applications incorporated herein by reference. This and other oxime ethers may therefore prove to be powerful and valuable pharmaceuticals.

In order to be useful as a pharmaceutical on a commercial scale, and to facilitate testing for regulatory approval, a target compound must be capable of economical synthesis and isolation in high yield and purity. Oxime ethers, for example, are capable of existing in both Z and E forms. As is the case with many pharmaceutically active compounds, only one isomer displays the desired pharmacological activity. However, the synthesis of oxime ethers generally results in a mixture of both Z and E isomers. Conversion of Z and E isomers can be accomplished under suitable conditions for certain oximes, although the mechanisms of the conversions are not well known. The barrier to isomerization has been reported as large, *J. AM. CHEM. SOC.*, 88, p. 2775 (1966).

Methods which have proven useful in oxime isomer conversions include photochemical conversion, A. Padwa et al., "Concentration Effects in the Photochemical Syn-Anti Isomerism of an Oxime Ether," *J. ORG. CHEM.*, 39 2361–2366 (1974); A. C. Pratt et al., "Photochemistry of the Carbon-Nitrogen Double Bond. Part I. Carbon—Nitrogen v.s. Carbon—Carbon Double Bond Isomerization in the Photochemistry of α, β-Unsaturated Oxime Ethers: the Benzylideneacetone Oxime O-Methyl Ether System", *J. CHEM. SOC.*, P1, 1691–1693 (1986); by thermal conversion, J. Biørgo et al., "Conformational and Electronic Effects on Imine Stereochemistry", *TET. LETT.*, 1747–1750 (1972); and acid catalysis, C. R. Hauser et al., "Syn-Anti Isomerism of p-Chlorobenzaldoxime with Boron Fluoride", *J. ORG. CHEM.*, 20 1491–1495 (1955); *J. MED. CHEM.*, op. cit. In addition, thermal conversion of syn to anti configurations of imines, oxime esters, and haloimines was reported by D. Y. Curtin et al., "Uncatalyzed syn-anti Isomerization of Imines, Oxime Ethers, and Haloimines", *J. AM. CHEM. SOC.*, 88 pp. 2775–2786 (1966). The general solvent preference is an anhydrous organic solvent. Biochemical resolution of oxime ethers was reported by M. Murakata et al., "Lipase-catalyzed Kinetic Resolution of Phenylcyclohexanone Oxime Ethers" *TETRAHEDRON:ASYMMETRY*, 5 (10) pp. 2019–2024 (1994). However, each of these methods generally results in the preparation of enriched isomer mixtures still containing an unacceptably large amount of the undesired isomer. As these compounds differ only in the stereochemical configuration about the oxime nitrogen, their separation is problematic.

Final purification of Z isomer-enriched oxime ether mixtures thus far has required chromatographic techniques such as medium or high pressure liquid chromatography. However, such chromatographic methods, while suitable for laboratory or semi-preparative separations, are ill-suited for commercial preparation of multi-kilogram quantities. Without an efficient, cost-effective means of purification, even the most promising pharmaceuticals cannot be commercialized.

It would be desirable to provide a process by which oxime ethers can be synthesized and isolated as the Z isomer in substantial purity without the use of chromatographic techniques. It would be further desirable to provide a process whereby isomerization of the Z isomer to the E isomer may be achieved simply and inexpensively and the Z isomer isolated in high purity with minimal processing steps.

SUMMARY OF THE INVENTION

It has now been surprisingly discovered that the coupling of a substituted hydroxylamine with an azabicycloketone to form a Z/E oxime ether mixture; the conversion of the Z/E oxime mixture to enrich the mixture in the Z isomer; and the isolation of the Z isomer, may be accomplished in high yield and in a cost-effective manner by conducting both the coupling and conversion in water, extracting the enriched Z isomer into an organic solvent, and crystallizing the pure Z isomer from an organic solvent. By selection of suitable conversion conditions and acid salt-forms, Z isomer purity in excess of 98% may be obtained. Importantly, the synthesis and isolation both take place without use of chromatographic techniques.

DESCRIPTION OF THE PREFERRED EMBODIMENTS

Coupling of substituted hydroxylamine and azabicycloketone takes place in water or a mixture of water and organic solvents. The O-substituted hydroxylamine component has the formula:

wherein R is preferably selected from $C_4$–$C_{12}$ aryl and substituted $C_4$–$C_{12}$ aryl, wherein the substituents are preferably alkoxy, i.e. methoxy, ethoxy, n-propoxy, or n-butoxy; halo, i.e. fluoro, chloro, bromo, or iodo; nitro; cyano; $C_{1-8}$ lower alkyl; $C_{2-8}$ alkenyl or alkynyl; $C_3$–$C_8$ cycloalkyl; $C_4$–$C_8$ cycloalkenyl; substituted lower alkyl, alkenyl, alkynyl, cycloalkyl, or cycloalkynyl, i.e. trifluoromethyl, chloromethyl, 2-cyanoethyl, and the like. Preferably, the aryl groups are selected from phenyl, naphthyl, and biphenyl. The aryl groups may also contain heteroatoms, i.e. may be heteroaromatic moieties such as pyridyl, quinolyl, etc. $C_4$ and $C_5$ aryl groups require the presence of one or more heteroatoms. Most preferred as R is m-methoxyphenyl. The most preferred O-substituted hydroxylamine is O-(m-methoxyphenylpropargyl)hydroxylamine.

The azabicycloketone is a 1-azabicyclo[2.2.1]heptan-3-one or a 1-azabicyclo[2.2.2]octan-3-one. Thus, the azabicycloketones correspond to those having the formula:

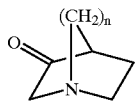

wherein n is 1 or 2, and where the stereochemical configuration is R, S or R/S when n is 1.

The coupling reaction is conducted in the presence of water, optionally in admixture with a minor amount of a soluble co-solvent such as methanol, ethanol, isopropanol, methylene chloride, dimethyl sulfoxide, and the like. Most preferably, the reaction medium consists substantially of water, i.e. without the presence of a water soluble co-solvent. The coupling reaction generally proceeds most rapidly under acidic conditions, but works well under neutral or even basic conditions as well. See, for example, J. March, *ADVANCED ORGANIC CHEMISTRY*, 3d Ed., p. 805–6, John Wiley & Sons, N.Y. (1985). Preferably, the coupling reaction takes place in the presence of an organic acid or mineral acid which also promotes conversion of E-oxime to Z-oxime, preferably an organic carboxylic acid. The presence of preferred organic acid is found to affect the Z/E equilibrium. The requisite quantities of strong acid and organic acid may be added separately to the reaction mixture, or may be incorporated in the form of the salt of the hydroxylamine and/or of the azabicycloketone. For example, acidic conditions may be established through addition of hydrochloric acid or through the use of the hydrochloride salt of the azabicycloketone. The isomerizing-promoting organic acid may be provided as the acid salt of the substituted hydroxylamine, i.e. as the oxalate when the organic acid is oxalic acid.

The coupling/isomerization is conducted at room temperature for a time sufficient to achieve the equilibrium Z/E mixture. This time will vary with the particular substrates, mineral acid, isomerizing acid, etc., but generally ranges from 4 hours to 24 hours, more preferably from 6 hours to 16 hours, and most preferably from 8 hours to 14 hours. Higher temperatures in combination with the isomerizing acid increase the rate of conversion to the enriched Z isomer mixtures.

Following coupling/isomerization, the reaction mixture is rendered alkaline to liberate the free base of the oxime ether addition product. The alkalinity may be provided by any base, e.g. sodium hydroxide, potassium hydroxide, alkali metal alkoxides, etc., but is preferably provided through use of carbonates or bicarbonates, i.e. a solution of potassium carbonate or sodium bicarbonate. The pH is advantageously raised to from 9 to 11, preferably about 10. The free base is then extracted with a solvent of limited water solubility. Examples of suitable solvents include methylene chloride, ethyl acetate, diethyl ether, hexane, tetrahydrofuran, toluene, and the like, although the preferred solvent is methyl-tert-butyl ether (MtBE).

Following extraction of the free base into the solvent, the enriched Z-isomer is isolated by adding one or more, preferably a single, solvent soluble acid. Acids that enrich the Z/E ratio into the 80–90/20—20 range include, but are not limited to acetic acid, butyric acid, t-butyric acid, L-(+)-lactic acid, 1-naphthalene carboxylic acid, 2-naphthalene carboxylic acid, fumaric acid, maleic acid, succinic acid, malic acid, oxalic acid, L-(+)-tartaric acid, propionic acid, stearic acid, undecanoic acid, citric acid, D-(−)-tartaric acid, benzenesulfonic acid, p-toluenesulfonic acid, N-acetylglycinic acid, saccharic acid, and p-nitrobenzoic acid. It has surprisingly been found that when the most preferred acid, benzoic acid, is utilized, Z-isomer purities of greater than 98%, generally greater than 99% are obtained. The pure Z isomer free base, if desired, may then be liberated by standard techniques.

The isolation of pure Z isomer by crystallization of the benzoate salt can occur in most common organic solvents (for example: diethyl ether, ethyl acetate, toluene, tetrahydrofuran, or methyl-tert-butylether or a combination of a polar and non-polar solvents such as methanol, ethanol, isopropanol, methylene chloride or chloroform and pentane, hexane or heptane). The preferred solvent of choice is methyl-tert-butylether because of the ease of combining the extraction and the following benzoate salt crystallization.

The inventive method performs coupling of the azabicycloketone with the hydroxylamine in water, resulting in a mixture of Z and E isomers. Using the appropriate acid in the reaction mixture results in the conversion of E to Z in the same solvent and pot as the coupling. Extraction of the free base into methyl-tert-butylether, cutting away the water layer, followed by addition of benzoic acid results in isolation by crystallization of the salt with substantially pure Z isomer. It is this combination of procedures that makes a simple and efficient process. It is the surprising discovery of this invention that, contrary to the teaching of prior art, both the coupling reaction and the Z to E conversion occur in water and the isolation of >98% Z isomer can be obtained by a salt crystallization.

The process may be illustrated by the reaction of 1-azabicyclo[2.2.1]heptan-3-one, R isomer, with O-(m-methoxyphenylpropargyl)hydroxylamine oxalate, as shown by the following reaction sequence:

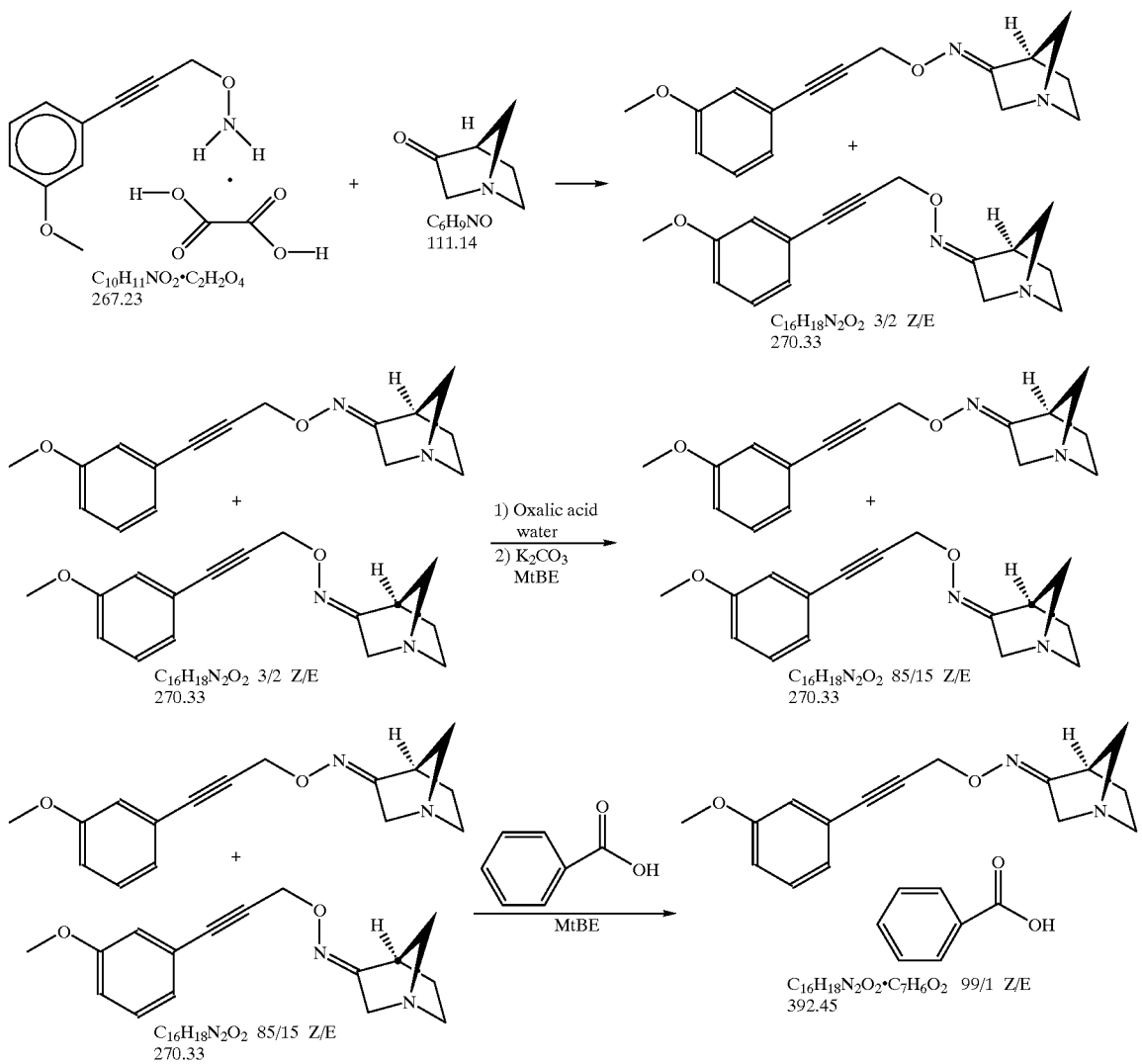

As indicated in the above sequence, the initial oxime synthesis results in a 3/2 (60:40) ratio of the Z isomer to the E isomer. Due to the conversion process which overlaps the synthesis and continues to the isolation of the free base in MtBE, the Z/E ratio is improved to 85:15. Isolation as the benzoate salt improves the isolated oxime ether Z/E ratio to about 99:1. The mother liquor contains further E isomer which may be converted to Z isomer and recrystallized to improve the overall yield of the process. The purity of the desired Z isomer is sufficient for use in pharmaceutical applications without use of expensive chromatographic separation.

Having generally described this invention, a further understanding can be obtained by reference to certain specific examples which are provided herein for purposes of illustration only and are not intended to be limiting unless otherwise specified.

EXAMPLE 1

Preparation of the [R-(Z)]-1-azabicyclo[2.2.1]
heptan-3-one, O-[3-(3-methoxyphenyl)-2-propynyl]
oxime, benzoate (1:1) salt 1-azabicyclo[2.2.1]heptan-3-one, R isomer, HCl salt (10.3 kg, 69.8 mol) was dissolved in 125.0 L water and added to 16.0 kg (69.8 mol) of O-(m-methoxyphenylpropargyl)hydroxylamine oxalate and stirred overnight at 20–25° C. The aqueous solution was pH adjusted to $\geq 10$ with a potassium carbonate solution (70 kg of potassium carbonate dissolved in 70 kg of water). The product was twice extracted with MtBE (56 kg and 28 kg), and the MtBE extracts combined. The organic MtBE solution was concentrated by vacuum distillation to an oil. The oil was dissolved in methyl-tert-butyl ether (75 kg) containing benzoic acid (7.0 kg, 57.3 mol) and the solution was heated to reflux for about 15 minutes. The solution was cooled to 45° C. and seed crystals added. The slurry was slowly cooled to 0° C. The crystalline product was collected by filtration.

For a second crop of product. 2.5 kg of oxalic acid and 36 L water were combined with the filtrate solution. The two phase mixture was stirred at reflux for 3 hours, cooled to 20–25° C., the pH adjusted to $\geq 10$, the product extracted into MtBE, concentrated by vacuum distillation and the crystallization process was repeated with 2.0 kg acid and 19 kg of MtBE. The crystalline product was collected by filtration.

The combined 1st and 2nd crop solids and 87 kg of MtBE were heated to reflux for 15 minutes, cooled to 45° C. and seed crystals added. The slurry was slowly cooled to 0° C. The crystalline product was dried at 40–45° C. under vacuum to obtain 20.6 kg of solid R-(Z)-1-azabicyclo[2.2.1]heptan-3-one, O-[3-(3-methoxyphenyl)-2-propynyl]oxime, benzoate (1:1) salt.

HPLC Assay: 99.53% Z-(R) and 0.05% E-(R) oxime isomers excluding benzoic acid. $^1$HNMR (CDCl$_3$): δ8.08 (d, J=6.7 Hz, 2H), 7.50 (m, 3H), 7.29–6.82 (m, 4H), 6.01 (br s, 1H), 4.83 (s, 2H), 3.78 (s, 3H), 3.68 (m, 1H), 3.44–3.12 (m, 3H), 2.94 (m, 1H), 2.78 (m, 2H), 2.08 (m, 1H), 1.78 (m, 1H).

EXAMPLE 2

Preparation of the [S-(Z)]-1-azabicyclo[2.2.1]heptan-3-one, O-[3-(3-methoxyphenyl)-2-propynyl]oxime, benzoate (1:1) salt (S)-1-azabicyclo[2.2.1]heptan-3-one, (96.5 g), 0.869 mol) and hydrogen chloride (37 g, 1.01 mol) in water (1560 ml) were stirred with O-(m-methoxyphenylpropargyl)hydroxylamine oxalate (225.2 g, 0.952 mol) at 22° C. for 22 hours. The aqueous solution was adjusted to pH>10 with sodium bicarbonate (qs) and washed with methyl-tert-butyl ether (2×1000 ml). The ether solution was heated to reflux with benzoic acid (100 g, 0.819 mol), concentrated by atmospheric distillation to 1 liter and cooled to −10° C. A first crop precipitate (265 g, 0.676 mol) was isolated by filtration at −10° C.

The filtrate was stirred with water (0.5 L) and oxalic acid (18 g, 0.2 mol) at reflux for 3.5 hrs and then cooled to 22° C. The solution was adjusted to pH>10 with sodium bicarbonate (qs), the aqueous layer was separated and the aqueous layer was washed with methyl-tert-butyl ether (250 ml). The ether layers were combined, heated to reflux with benzoic acid (24 g, 0.197 mol), concentrated by atmospheric distillation to 0.2 liters and cooled to −10° C. A second crop precipitate (41.7 g, 0.106 mol) was isolated by filtration at −10° C.

The solid precipitates (297.8 g, 0.749 mol) were combined and recrystallized two times from methyl-tert-butyl ether (1470 ml, 1500 ml) and dried under reduced pressure to yield the [S-(Z)]-1-azabicyclo[2.2.1]heptan-3-one, O-[3-(3-methoxyphenyl)-2-propynyl]oxime, benzoate salt (1:1, (263.3 g, 0.671 mol).

HPLC Assay: 99.82% Z-(S) and 0.19% E-(S) oxime isomers excluding benzoic acid. $^1$HNMR (CDCl$_3$): δ8.08 (m, 2H), 7.44 (m, 3H), 7.20 (t, 1H), 7.02 (m, 2H), 6.86 (m, 1H), 4.83 (s, 2H), 3.81 (t, 1H), 3.74 (s, 3H), 3.44 (m, 1H), 3.26 (m, 2H), 2.96 (d, 1H), 2.78 (m, 2H), 2.03 (m, 1H), 1.76 (m, 1H), 0.37 (s, 1OH).

EXAMPLE 3

Preparation of the [R,S-(Z)]-1-Azabicyclo[2.2.1]heptan-3-one, O-[3-(3-methoxyphenyl)-2-propynyl]oxime, benzoate (1:1) salt (R,S)-1-Azabicyclo[2.2.1]heptan-3-one, (7.0 g, 0.063 mol) and hydrogen chloride (2.3 g, 0.063 mol) in water (125 ml) were stirred with O-(methoxyphenylpropargyl)hydroxylamine oxalate (14.5 g, 0.063 mol) at 22° C. for 18 hours. The aqueous solution was adjusted to pH>10 with sodium bicarbonate (qs) and washed with methyl-tert-butyl ether (3×120 ml). The ether solution was concentrated to an oil (15.7 g, 0.058 mol). The oil was dissolved in methyl-tert-butyl ether (70 g) containing benzoic acid (6.4 g), 0.524 mol). The mixture was heated to reflux and cooled to 22° C. A solid precipitate (16.3 g, 0.0415 m) was isolated by filtration at 22° C. The solid was recrystallized three times from methyl-tert-butyl ether (70 g, 50 g, 30 g) and dried under reduced pressure to yield the [R,S-(Z)-1-azabicyclo[2.2.1]heptan-3-one-O-[3-(3-methoxyphenyl)-2-propynyl]oxime, benzoate salt (1:1), (4.62 g, 0.012 mol).

HPLC Assay: 99.02% Z-(R/S) and 0.98% E-(R/S) oxime isomers excluding benzoic acid. $^1$HNMR (CDCl$_3$); δ8.63 (s, 10H), 8.06 (t, 2H), 7.47 (m, 3H), 7.22 (m, 1H), 7.03 (m, 2H), 6.88 (m, 1H), 4.83 (s, 2H), 3.79 (s, 3H), 3.69 (s, 1H), 3.22 (m, 3H) 2.93 d, 1H), 2.76 (m, 2H), 2.06 (m, 1H), 1.78 (m, 1H).

EXAMPLE 4

Preparation of the (Z)-1-azabicyclo[2.2.2]octan-3-one, O-[3-(3-methoxyphenyl)-2-propynyl]oxime, benzoate (1:1) salt 3-Quinuclidinone (4.0 g, 0.0265 mol) in water (30 ml) was stirred with O-(m-methoxyphenylpropargyl) hydroxylamine oxalate (6.2 g, 0.0248 mol) at 22° C. for 20 hours. The aqueous solution was adjusted to pH>10 with sodium bicarbonate (qs) and washed with methyl-tert-butyl ether (2×40 ml). The ether solution was concentrated under reduced pressure to yield a yellow oxime oil (6.74 g, 84.7%). The oil (6.74 g) was dissolved in methyl-tert-butyl ether (50 ml) containing benzoic acid (2.5 g, 0.0205 m). The mixture was heated to reflux and then cooled to 22° C. A solid precipitate (7.16 g, 0.0162 mol) was isolated by filtration at 22° C. The solid was recrystallized two times from methyl-tert-butyl ether (2×46 ml) and dried under reduced pressure to yield the 1-azabicyclo[2.2.2]octan-one, O-[3-(3-methoxyphenyl)-2-propynyl]oxime, benzoate (5.67 g, 51.7%).

$^1$HNMR (CDCl$_3$): δ12.8 (br s, 1H), 8.0 (m, 2H), 7.43 (m, 3H), 7.20 (m, 1H), 7.03 (m, 2H), 6.94 (m, 1H), 4.85 (s, 2H), 3.88 (s, 2H), 3.78 (s, 3H), 3.11 (m, 4H), 2.77 (m, H), 1.95 (m, 4H) CHN assay calculated for $C_{17}H_{20}N_2O_2C_7H_6O$, C=71.00% (70.92), H=6.39% (6.45), N=6.82 (6.89). MP 93.7–95.0° C.

HPLC Assay: 99.41% Z and 0.59% E oxime isomers excluding benzoic acid.

By the unadorned term "acid" is meant both organic acids and mineral acids. By the term "effective to enrich" with reference to the Z isomer is meant an acid in a quantity sufficient to cause an enriched concentration of Z-isomer (Z/E ratio) as compared to the concentration obtainable in the absence of an effective enriching amount. By the term "contemporaneously or sequentially" is meant that the enriching acid may be added together with the O-substituted hydroxylamine, for example as the free acid or as the salt of the hydroxylamine, or subsequently after the initial coupling has been concluded. By the term "O-R" substituted azabicyclooxime ethers" and like terms is meant the reaction product of the substituted hydroxylamine and the azabicycloketone, having a substituent on the oxygen atom of the oxime ether linkage. For example, when O-(m-methoxyphenylpropargyl)hydroxylamine is the O-substituted hydroxylamine, the O-substituted oxime ether will have the m-methoxyphenylpropargyl group as the substituent.

Having now fully described the invention, it will be apparent to one of ordinary skill in the art that many changes and modifications can be made thereto without departing from the spirit or scope of the invention as set forth herein.

What is claimed is:

1. A process for the isolation of azabicyclo oxime ethers in high Z purity, said process comprising:

a) reacting an O-substituted hydroxylamine having the formula

wherein R is substituted or unsubstituted $C_{4-12}$ aryl or heteroaryl;
with an azabicycloketone having the formula:

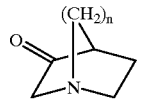

wherein n=1 or 2, and where the stereochemical configuration is R, S, or R/S when n is 1;
in aqueous solution to form a product mixture of Z and E isomers of —$CH_2$—C≡C—R substituted azabicyclooxime ethers;

b) contemporaneously or sequentially adding one or more acids effective to enrich said product mixture in the Z-isomer of said —$CH_2$—C≡C—R substituted azabicyclooxime ether;

c) raising the pH of said product mixture to a pH effective to liberate the free base of said —$CH_2$—C≡C—R substituted azabicyclooxime ether;

d) extracting said free base with a non-aqueous solvent of limited aqueous solubility;

e) adding a salt-forming acid to said free base dissolved in a non-aqueous solvent; and f) recovering a substantially pure (Z) azabicyclooxime ether salt.

2. The process of claim 1 wherein the substituent of said substituted aryl or heteroaryl group is selected from the group consisting of alkoxy; halo; $C_{1-8}$ lower alkyl; $C_{2-8}$ alkenyl; $C_{2-8}$ alkynyl; $C_{3-8}$ cycloalkyl; $C_{4-8}$ cycloalkenyl; and mixtures thereof.

3. The process of claim 1 wherein R is m-methoxyphenyl.

4. The process of claim 1 wherein said aqueous solution is substantially devoid of organic solvents.

5. The process of claim 1 wherein said organic acid is selected from the group consisting of organic carboxylic acids.

6. The process of claim 5 wherein said organic carboxylic acid is oxalic acid.

7. The process of claim 1 wherein said salt-forming acid is an organic or mineral acid.

8. The process of claim 7 wherein said organic acid comprises benzoic acid.

9. The process of claim 1 wherein said process does not employ chromatographic purification and/or separation.

10. The process of claim 1 wherein the Z/E isomer mol ratio of said Z and E isomers of said isolated —$CH_2$—C≡C—R substituted azabicyclo oxime ether is greater than 95:5.

11. The process of claim 1 wherein the Z/E isomer mol ratio of said Z and E isomers of said isolated —$CH_2$—C≡C—R substituted azabicyclo oxime ether is greater than 98:2.

12. The process of claim 1 wherein said pH effective to liberate said free base is greater than 9.

13. The process of claim 1 wherein said pH effective to liberate said free base is about 10 or more.

14. The process of claim 1 wherein said solvent of limited aqueous solubility for extraction comprises methyl-tert-butyl ether.

15. The process of claim 1 wherein said step of recovering takes place in a solvent comprising an organic solvent.

16. The process of claim 1 wherein said step of recovering takes place in a solvent comprising methyl-tert-butyl ether.

17. The process of claim 1 wherein n is 1.

18. The process of claim 1 wherein n is 1 and said azabicycloketone stereochemistry configuration is R.

19. A process for the isolation of azabicyclo oxime ethers in high Z purity, said process comprising:

a) reacting an O-substituted hydroxylamine having the formula

wherein R is substituted or unsubstituted $C_{4-12}$ aryl or $C_{4-12}$ heteroaryl;
with an azabicycloketone having the formula:

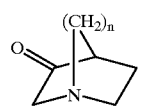

wherein n=1 or 2, and where the stereochemical configuration is R, S, or R/S wherein n is 1;
in aqueous solution to form a product mixture of Z and E isomers of —$CH_2$—C≡C—R substituted azabicyclooxime ethers;

b) contemporaneously or sequentially adding one or more acids effective to enrich said product mixture in the Z-isomer of said —$CH_2$—C≡C—R substituted azabicyclooxime ether;

c) raising the pH of said product mixture to a pH of about 9 or more to liberate the free base of said —$CH_2$—C≡C—R substituted azabicyclooxime ether;

d) extracting said free base with methyl-t-butyl-ether solvent;

e) adding benzoic acid to said free base dissolved in said methyl-tert-butyl ether solvent; and f) recovering a substantially pure (Z) isomer of an R-substituted azabicyclooxime ether benzoate salt.

20. A process for the isolation of [R-(Z)-1-azabicyclo[2.2.1]heptan-3-one, O-[3-(3-methoxyphenyl)-2-propynyl]oxime in high purity, said process comprising:

a) reacting O-(m-methoxyphenylpropargyl)hydroxylamine with [R]-1-azabicyclo[2.2.1]heptan-3-one in aqueous solution;

b) adding contemporaneously or sequentially oxalic acid as the free acid or as the oxalate salt of O-(m-methoxyphenylpropargyl)hydroxylamine;

c) adding sufficient base to raise the pH of the aqueous reaction mixture to a pH of 9 or higher;

d) extracting the free base of [R]-1-azabicyclo[2.2.1]heptan-3-one, O-[3-(3-methoxyphenyl)-2-propynyl]oxime with methyl-tert-butyl ether;

e) adding benzoic acid to a solution of said free base in methyl-tert-butyl ether;

f) collecting from said solution prepared in step (e) the benzoate salt of [R-(Z)-1-azabicyclo[2.2.1]heptan-3-one, O-[3-(3-methoxyphenyl)-2-propanyl]oxime in a purity in excess of 90%.

* * * * *